United States Patent
Beymer et al.

(10) Patent No.: US 9,436,995 B2
(45) Date of Patent: Sep. 6, 2016

(54) DISCRIMINATING BETWEEN NORMAL AND ABNORMAL LEFT VENTRICLES IN ECHOCARDIOGRAPHY

(71) Applicant: INTERNATIONAL BUSINESS MACHINES CORPORATION, Armonk, NY (US)

(72) Inventors: David J. Beymer, San Jose, CA (US); Patrick K. McNeillie, Campbell, CA (US); Tanveer F. Syeda-Mahmood, Cupertino, CA (US); Quan Wang, Troy, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 61 days.

(21) Appl. No.: 14/262,780

(22) Filed: Apr. 27, 2014

(65) Prior Publication Data
US 2015/0310612 A1    Oct. 29, 2015

(51) Int. Cl.
*G06T 7/00* (2006.01)
*G06K 9/62* (2006.01)

(52) U.S. Cl.
CPC ........... *G06T 7/0014* (2013.01); *G06K 9/6207* (2013.01); *G06K 9/6209* (2013.01); *G06K 9/6269* (2013.01); *G06T 2207/10132* (2013.01); *G06T 2207/30048* (2013.01)

(58) Field of Classification Search
CPC .................. G06T 2207/30048; G06T 7/0012; G06T 7/0089; G06T 2207/10132; G06T 7/0083; G06T 7/001; G06T 7/0014; G06T 7/0081
See application file for complete search history.

(56) References Cited

U.S. PATENT DOCUMENTS

| | | | | |
|---|---|---|---|---|
| 5,734,739 A | * | 3/1998 | Sheehan | G06T 7/0012 382/128 |
| 6,106,466 A | * | 8/2000 | Sheehan | A61B 5/1075 128/916 |
| 6,788,827 B1 | * | 9/2004 | Makram-Ebeid | G06T 7/2033 382/276 |

(Continued)

OTHER PUBLICATIONS

Nandagopalan et al., "A Naive Bayesian Methodology to Classify Echo Cardiographic Images through SQL" in Knowlege, Information, and Creativity Support Systems of the series LNCS, 2011 [retrieved May 18, 2016], Springer Berlin Heidelberg, vol. 6746, pp. 155-165. Retrieved from the Internet http://link.springer.com/chapter/10.1007/978-3-642-24788-0_15.*

(Continued)

*Primary Examiner* — Matthew Bella
*Assistant Examiner* — Dennis Rosario
(74) *Attorney, Agent, or Firm* — Erik Huestis; Stephen Kenny; Foley Hoag LLP

(57) ABSTRACT

Embodiments of the present invention relate to discriminating between normal and abnormal left ventricles in echocardiography. In one embodiment, a method of and computer program product for discriminating between normal and abnormal left ventricles in echocardiography are provided. A first region of a first image of a heart is located. The first region depicts a chamber of the heart. A boundary of the first region is determined. A predetermined shape is compared to the boundary. A first plurality of parameters is determined that, when applied to the predetermined shape, conforms the predetermined shape to the boundary. The first plurality of parameters is provided to a classifier. An indication of normality or abnormality is received from the classifier.

20 Claims, 13 Drawing Sheets

(56) References Cited

U.S. PATENT DOCUMENTS

| | | | |
|---|---|---|---|
| 7,110,583 B2 * | 9/2006 | Yamauchi | G06F 19/3437 |
| | | | 128/915 |
| 7,558,402 B2 | 7/2009 | Zhou | |
| 7,620,205 B2 | 11/2009 | Zhou | |
| 7,668,354 B2 * | 2/2010 | O'Donnell | G01R 33/563 |
| | | | 378/4 |
| 7,668,370 B2 | 2/2010 | Noble | |
| 8,265,363 B2 | 9/2012 | Orderud | |
| 8,280,136 B2 * | 10/2012 | Gotardo | G06K 9/6207 |
| | | | 378/4 |
| 2003/0035573 A1 * | 2/2003 | Duta | G06K 9/62 |
| | | | 382/128 |
| 2003/0038802 A1 | 2/2003 | Johnson | |

OTHER PUBLICATIONS

Wang et al. (2013) "Learning-Based Detection and Tracking in Medical Imaging: A Probabilistic Approach." In Deformation Models, Springer Netherlands pp. 209-235.

Fernandez-Caballero, A. & Vega-Riesco, J.M. (2009) "Determining heart parameters through left ventricular automatic segmentation for heart disease diagnosis." Expert Systems with Applications 36, No. 2, 2234-2249.

Guo et al. (2013) "Automatic Segmentation of Fetal Echocardiogram Using Modified Active Appearance Models and Sparse Representation." DOI 10.1109/TBME.2013.2295376, IEEE Transactions on Biomedical Engineering.

* cited by examiner

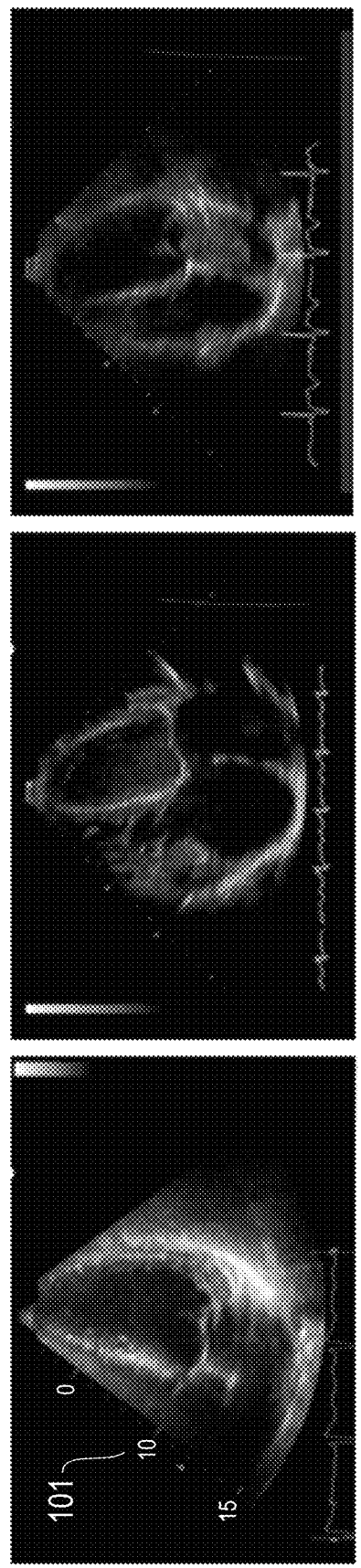

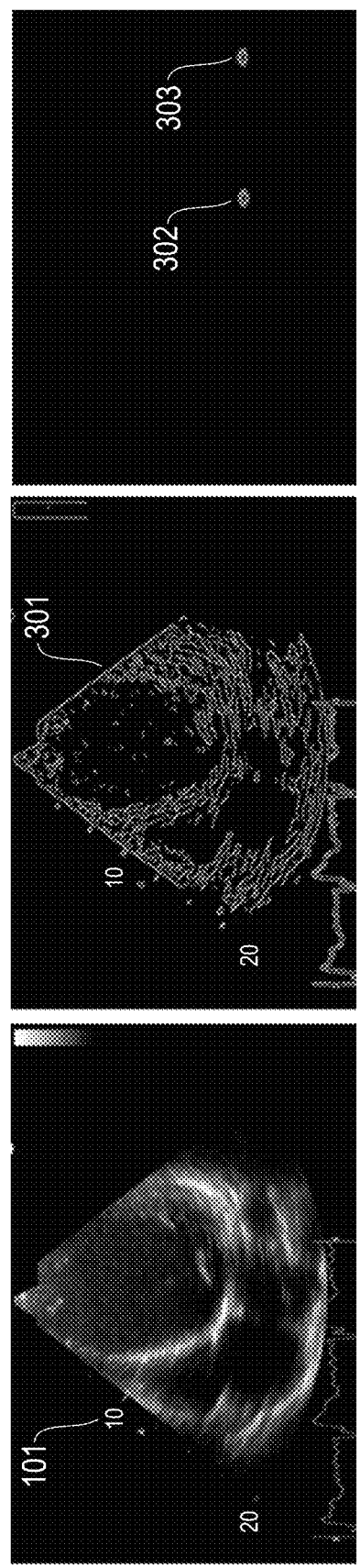

DISCRIMINATING BETWEEN NORMAL AND ABNORMAL LEFT VENTRICLES IN ECHOCARDIOGRAPHY

BACKGROUND

Embodiments of the present invention relate to analysis of echocardiograms, and more specifically, to discriminating between normal and abnormal left ventricles in echocardiography.

BRIEF SUMMARY

According to one embodiment of the present invention, a method of and computer program product for discriminating between normal and abnormal left ventricles in echocardiography are provided. A first region of a first image of a heart is located. The first region depicts a chamber of the heart. A boundary of the first region is determined. A predetermined shape is compared to the boundary. A first plurality of parameters is determined that, when applied to the predetermined shape, conforms the predetermined shape to the boundary. The first plurality of parameters is provided to a classifier. An indication of normality or abnormality is received from the classifier.

BRIEF DESCRIPTION OF THE SEVERAL VIEWS OF THE DRAWINGS

FIGS. 1A-C depict exemplary normal left ventricle shapes.

FIGS. 3A-I illustrate localization and matching of the left ventricle bounding contour with parametric distorted ellipses according to embodiments of the present disclosure.

DETAILED DESCRIPTION

Figure 1D:
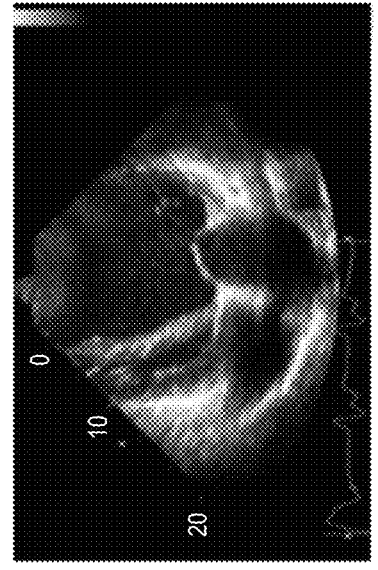
FIGS. 1D-F depict exemplary abnormal left ventricle shapes caused by disease.
Figure 1E:
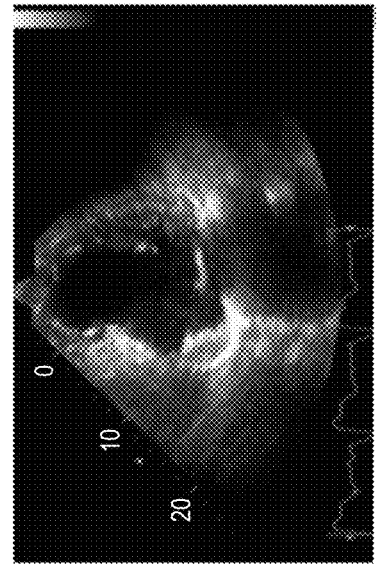
Figure 1F:
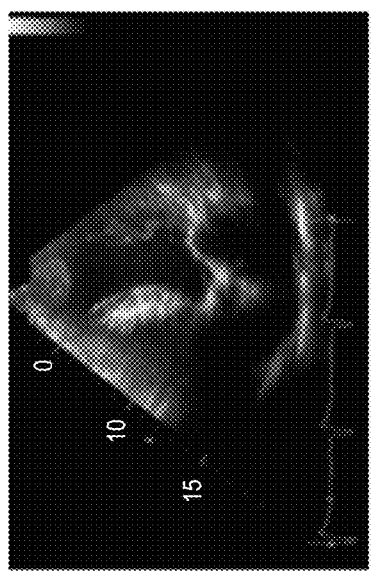
Figure 2C:
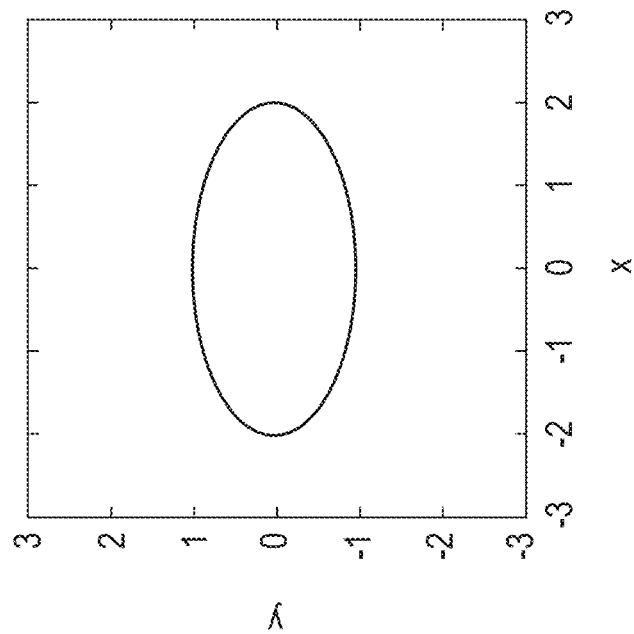
FIGS. 2A-E depict exemplary shapes of a distorted ellipse model according to embodiments of the present disclosure.
Figure 2B:
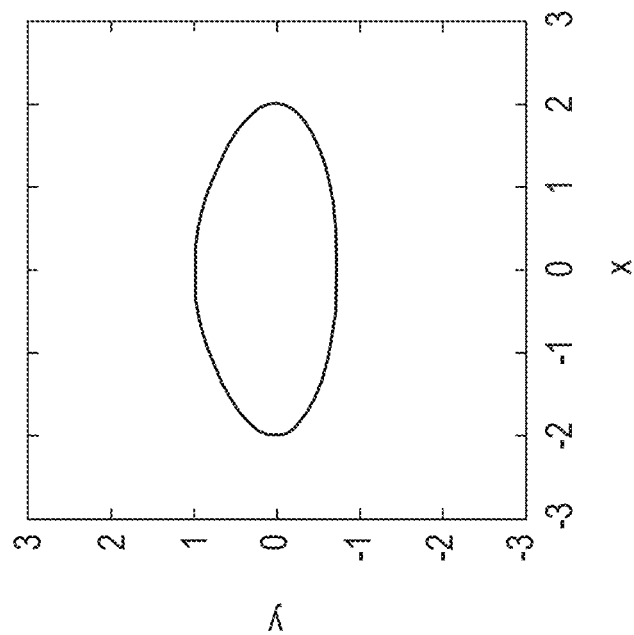
Figure 2A:
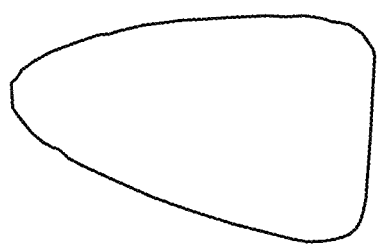
Figure 2E:
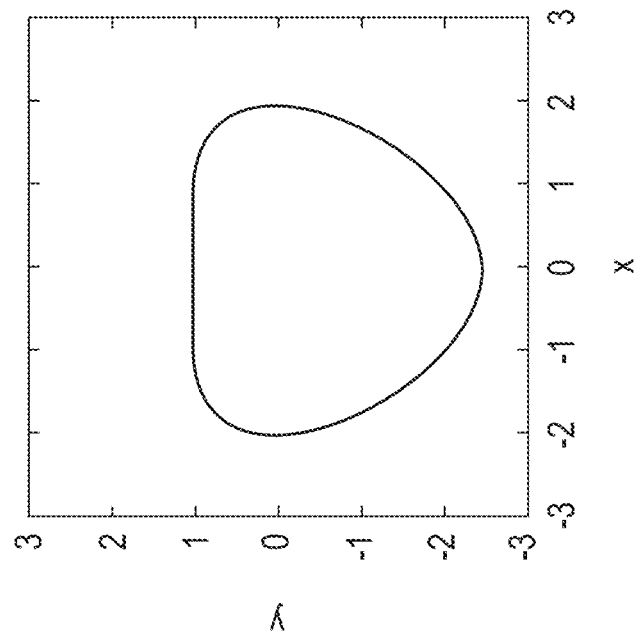
Figure 2D:
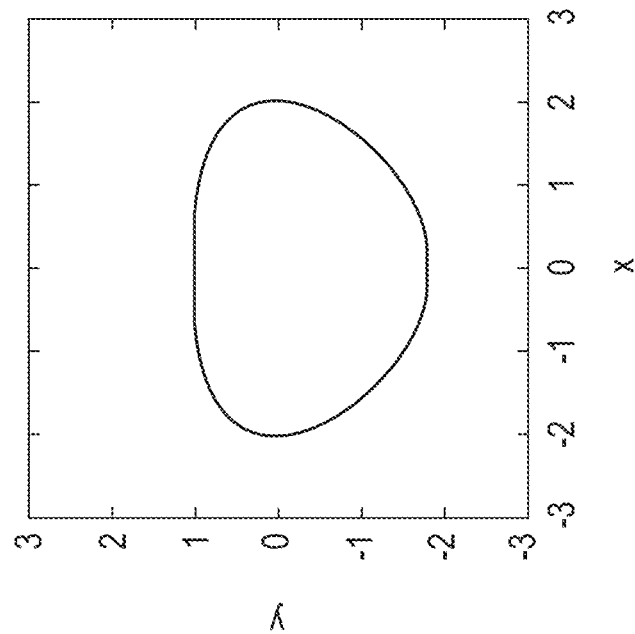

The study of left ventricular shape and function is important in 2D echocardiography. Impairment to left ventricular shape and structure affects cardiac function and is often seen in several cardiac diseases such as aneurysms, cardiomyopathies and infarctions. FIG. 1 illustrates the difference in the appearance of the left ventricle (LV) in normal and diseased cases, with FIGS. 1A-C showing normal LV shapes and FIGS. 1D-F showing distorted LV shapes due to diseases such as cardiomyopathies (FIG. 1D) and aneurysms (FIGS. 1E-F). While even normal ventricular shape is influenced by many factors including the patient's physiognomy and the chest configuration, a grossly abnormal geometry of a ventricle may indicate the presence of a pathology. While a patient with normally appearing left ventricle (LV) could still have cardiac disease (e.g., FIG. 1E), it is still worthwhile to examine the shape of this prominent chamber to develop an understanding of many cardiac diseases and to build automated clinical decision support systems.

According to various embodiments of the present disclosure, systems, methods and computer program products are provided for discriminating between normal and abnormal left ventricles. Deviations are captured from the normal appearance through a parametric distorted elliptic shape model. The parameters of the distortion as well as the overall fit of the distorted ellipse to a given left ventricular bounding contour are used to form feature vectors to classify between normal and abnormal LV shapes using a support vector machine. Since the accuracy of discrimination depends on the accuracy of localization of the left ventricular bounding contour in images, an automatic method is provided for extracting such contours from 4-chamber view echocardiographic sequences. To enable robust classification due to the changing shape of the left ventricle within a heart cycle, the temporal information in the sequence is incorporated using parametric features from all images of the sequence per study. Applying the present subject matter to a large database of echocardiographic sequences indicates that the features derived from parametric fits of these distorted ellipses allows discrimination between normal and abnormal left ventricular shapes.

Various embodiments of the present disclosure use the parametric distorted elliptic shape model described further below. However, various alternative embodiments use other descriptions of the left ventricular shape. In some such embodiments, measurements may be used such as area-length from prolate ellipsoidal representations using ellipsoids manually isolated by echocardiographers. In other such embodiments, the left ventricular (LV) shape is modeled using a variety of techniques including active shape and appearance models, snakes and active contours, parametric shape descriptors of endocardial contours, deformable models and templates, and level set techniques.

Some model-based approaches such as active shape models may be difficult to learn from a class of shapes, as they require manual marker identification as well as prior registration of shapes during model training Such models, when used to both localize and recognize the left ventricle, may have localization errors. Therefore, in some embodiments, the bounding contours of the left ventricle are first localized in a bottom-up fashion before fitting the distorted ellipsoidal model. A similar process may be used for active contour and active snakes model fitting. However, models allow greater flexibility in warping of shapes. This unconstrained flexibility can be a barrier in estimating the extent to which shapes deviate from expected normal appearance.

The normal shape of the left ventricle may be described as a bullet or a prolate ellipsoid in three dimensions. However, as seen in FIG. 1, cardiac diseases result in considerable deviations from this shape. According to embodiments of the present disclosure, these distortions are formulated as deviations from the prolate ellipsoidal shape. Specifically, by restricting to 4-chamber views in B-mode 2D echocardiography, a new parametric description is formulated for a 2D projection of the LV as a distorted ellipse $C_{a,b,p}(x,y)$ given by Equation 1.

$$\begin{bmatrix} x \\ y \end{bmatrix} = s \cdot R \begin{bmatrix} a \cdot \cos\theta \\ b(1 - (1 - \sin\theta)^p) \end{bmatrix} + T \quad \text{Equation 1}$$

In Equation 1, $$R = \begin{bmatrix} \cos\varphi & -\sin\varphi \\ \sin\varphi & \cos\varphi \end{bmatrix}$$

is the rotation matrix capturing the global orientation of the left ventricular shape ϕ, s is the scale factor, and $$T = \begin{bmatrix} x_c \\ y_c \end{bmatrix}$$

is the global translation to position the shape on the centroid of the left ventricle. Here the core shape of the left ventricle is described by the parameters (a,b,p) where a and b are axes of the ellipse, the parameter p controls the distortion, and θ generated the points along the elliptical contour. Because the left ventricle is independently located in a prior region selection step, the similarity transform parameters (s,R,T) themselves are recovered from the orientation and centroid of the detected left ventricle. The scale is recovered from the calibration information in images as described further below.

Referring now to FIGS. 2A-E, a variety of plausible left ventricular shapes are shown. Each shape is produced by varying the parameters (a,b,p). As set forth further below, normal hearts are well-modeled through distinct parameter settings of (a,b,p). Abnormal left ventricles are modeled by other parameter ranges of (a,b,p) when they fit well (as in the case of dilated cardiomyopathy) or have large fit errors for even the best-fitting ellipses (as in the case of aneurysms).

Given a left ventricular bounding contour b (x',y') detected in an image, features are extracted for discriminating between normal and abnormal LV shapes as follows. Using the values of (R,T) from the LV region localization, the parametric distorted ellipse model is centered. Several candidate parametric shape $C_{a,b,p}(x,y)$ are generated by varying (a,b,p). For each such generated distorted ellipse contour, the alignment error is determined with the underlying LV bounding contour according to Equation 2.

$$E(C_{a,b,p}(x,y), b(x',y')) = \frac{|\langle x_m, y_m, x'_m, y'_m \rangle|}{|C_{a,b,p}(x,y)|} \quad \text{Equation 2}$$

In Equation 2, $|x_m-x_m'|<\delta$ and $|y_m-y_m'|<\delta$ are the nearest matched pair of points on the respective binary contours, with δ ranging from 1 to 3 pixels. The length of the parametric curve $|C_{a,b,p}(x,y)|$ in pixel coordinates is a function of (a,b,p) and (R,T) and can be measured at the time of synthesis within the image of projection.

By applying this parametric fit to every image in the echocardiographic sequence, a set of feature vectors is obtained per sequence S as F(S)={$f_i(S)$} as shown in Equation 3.

$$f_i(S) = \langle a_i, b_i, p_i, E_{mi}(C_{a_i,b_i,p_i}, B_i) \rangle \quad \text{Equation 3}$$

In Equation 3, $\langle a_i, b_i, p_i \rangle = \arg\min (E_i(C_{a_i,b_i,p_i}, B_i))$ and $E_{mi}(C_{a_i,b_i,p_i}, B_i)$ is the minimum alignment error. Using the ground truth normal/abnormal labels provided for the underlying echocardiographic sequences during training, a support vector machine (SVM) is used to separate the feature vectors of the normal from abnormal data. Given a new image, its feature vector is then classified using the learned SVM model. To enable robust classification due to the changing shape of the left ventricle within a heart cycle, the temporal information is incorporated in the sequence using parametric features from all images of the sequence per study. The majority vote from the feature vectors is then used to classify the left ventricle in a sequence as being normal or abnormal.

The search for the parametric fit can be kept contained by pre-analyzing the ranges of values of the fit in the training data. In one exemplary embodiment, the ranges of these values were analyzed in a training set of 800 echocardiogram images that showed shape variations of the left ventricle across patients and diseases. Let the size of the bounding box for the LV bounding contour be denoted by $N_x \times N_y$, where $N_x$ and $N_y$ are derived from the eigenvalues of the shape. The search ranges of the parameters are chosen as $a \in [0.3N_x, 0.4N_x]$, $b \in [0.15N_y, 0.25N_y]$, and p=[1.7,2.7].

Alternative LV segmentation methods such as region-based approaches may over- or under-segment the left ventricle, particularly in diseased cases. This results in inaccurate boundaries for initiating shape matching. Active shape model approaches to localize LV may have poor performance, locating the left ventricle accurately in only about 35% of the cases of 4-chamber views. Accordingly, a bottom-up approach to LV detection is provided that selects the nearest region to the intersection point of the region of interest (ROI) sector lines in apical 4-chamber views as follows.

Referring now to FIG. 3, ROI detection according to various embodiments of the present disclosure is illustrated. The ultrasound scan sector in the image (FIG. 3A) is usually bounded by dominant lines 301 as shown by the edge image of FIG. 3B. Using a Hough transform in polar coordinates (r,t) on the edge image, the dominant orientation is determined with maximum hits in the Hough transform. The intersecting lines bounding the sector are then found as pairs of high intensity spots 302, 303 in the Hough transform image as shown in FIG. 3C. The intersecting lines have the same r separated by ∂t (horizontal axis) corresponding to the sector angle.

The scale is estimated from the calibration markers and number units often present along the sector lines 101. The numbers are recognized through an optical character recognition (OCR) algorithm. Using the recognized units, the distance between markers is then converted to mm from pixel coordinates.

Figure 3F:
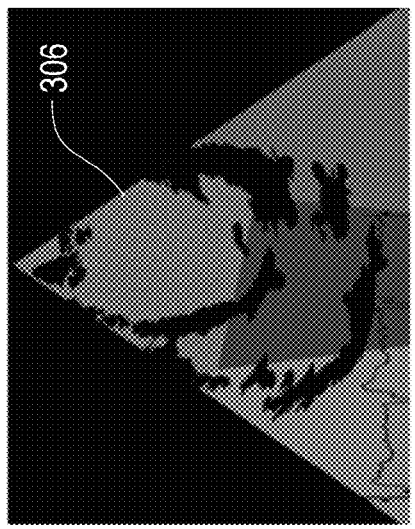
Figure 3E:
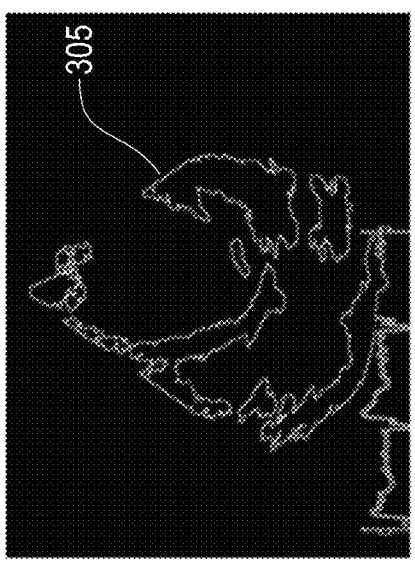
Figure 3D:
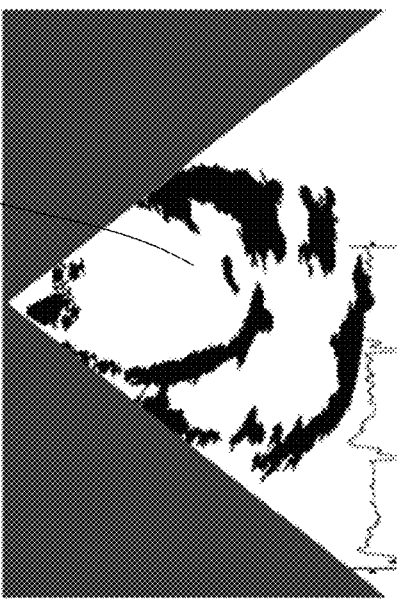

Referring to FIG. 3D, region thresholding is next performed. In some embodiments, the intensity gradients in the sector region are thresholded using adaptive Otsu thresholding. FIG. 3D shows the resulting image where the heart structure 304 is clearly highlighted.

According to various embodiments, LV localization is performed by clustering. To obtain a rough region containing the left ventricle, the triangular region defined by the intersecting sector lines and image borders is partitioned into regions using K-means clustering on the pixel locations in the thresholded binary image. Since four main chambers are usually seen in apical 4-chamber views, a value of K=4 is sufficient to separate the LV region from other regions included in the sector triangle. The region closest to the point of intersection of the sector lines is then taken as a rough indication of the location of the left ventricle as shown in FIG. 3F.

Figure 3I:

According to various embodiments, contour tracing is performed. By tracing the boundary pixels as curvilinear structures, sufficiently accurate contours 305 of the heart muscle and hence the LV bounding contours are obtained, as shown in FIG. 3E. The bounding contours that overlap the indicated LV region 306 from clustering, are then retained as shown in FIG. 3G. To avoid false matches to contours that are parallel to the (inner) LV contour such as the myocardium, the contours in the LV region are further limited by only retaining the nearest contours surrounding the region centroid as shown in FIG. 3I. Since the parametric fit is initiated from the distorted ellipse model, small fragmentation from such retention can be tolerated during the matching. When the LV contour is not fully visible, as can be seen in FIG. 3A, it poses a challenge. To provide robustness to such changes in the contour within the heart cycle, the best parametric fit is considered for every frame of the sequence forming the set of feature vectors for use in normal/abnormal classification.

Figure 3H:
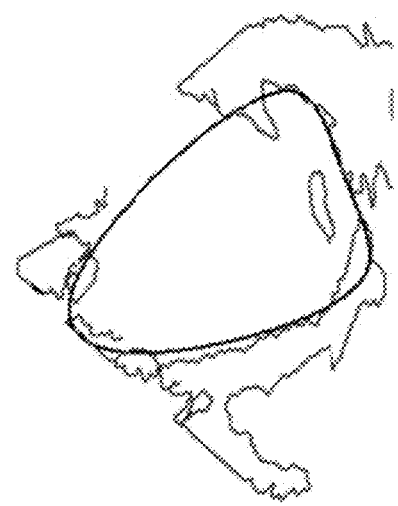
Figure 3G:
Figure 4A:
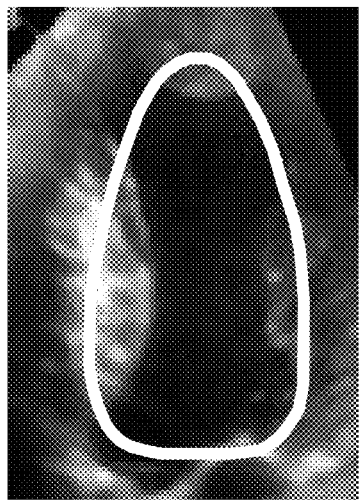
FIG. 4A-G illustrate parametric fits to the left ventricle in both normal and abnormal cases according to embodiments of the present disclosure.
Figure 4B:
Figure 4C:
Figure 4D:
Figure 4E:
Figure 4F:
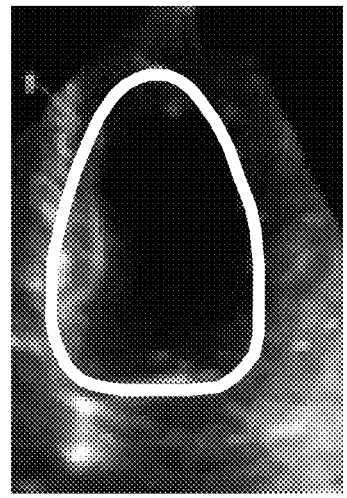
Figure 4G:
Figure 5A:
FIGS. 5A-F illustrate ground truth generation for left ventricle extraction according to embodiments of the present disclosure.
Figure 5B:
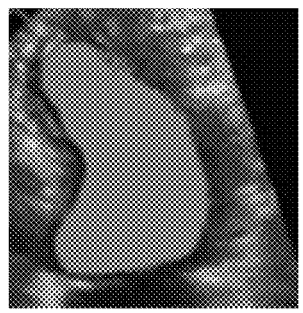
Figure 5C:
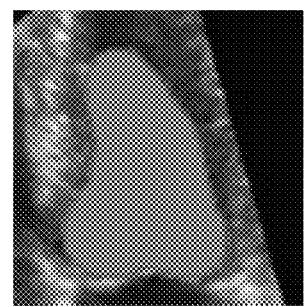
Figure 5D:
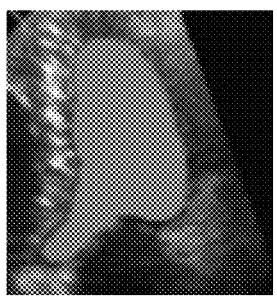
Figure 5E:
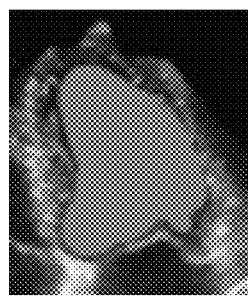
Figure 5F:
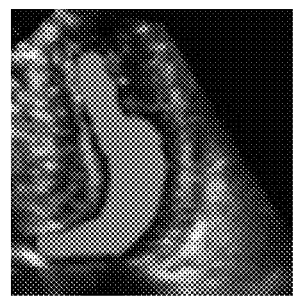

Referring now to FIG. 3H, the results of parametric fitting to left ventricles are illustrated. Using the centroid and orientation of the region, the best matching parametric fit for the left ventricle in FIG. 3A is shown in FIG. 3H. In this case, the patient has dilated cardiomyopathy and the LV resembles a bullet but the ellipsoidal parameters are significantly different from ranges for normal LV, which can also be seen from the large aspect ratio.

Referring to FIGS. 4A-G, exemplary results of matching of distorted ellipses to normal and abnormal left ventricles are provided.

Exemplary results of discrimination between normal and abnormal left ventricular shapes in 4-chamber views of echocardiographic sequences are provided below. This exemplary dataset consists of a total of 340 patients and 2158 echocardiographic sequences depicting a variety of cardiac diseases in patients ranging from aneurysms (89), dilated cardiomyopathy (76), hypertrophies (78) and normal LV size and function (448). Of these, 503 sequences are 4-chamber views including about 138 sequences labeled as normal LV size and function from their corresponding reports.

To discriminate between normal and abnormal LV, 40% of the normal and abnormal LV cases were used for training and the remaining for testing. A total of 25020 feature vectors were generated from these sequences as they were of variable length in heart cycles and averaged about 64 images per sequence. Different kernels for learning with support vector machines were applied, and the best classification performance was obtained with radial basis functions as kernels. The class was decided at the level of the echocardiographic sequence by taking the majority vote from the classification of parametric features of individual images of the sequence within cardiac cycles. The results are summarized in Table 1, which shows the accuracy of normal/abnormal discrimination of left ventricular shapes.

TABLE 1

| Classifier | Accuracy (%) |
|---|---|
| Fisher LDA | 68.92 |
| Linear SVM | 74.26 |
| RBF kernel SVM | 82.67 |
| kNN, k = 1 | 64.12 |
| kNN, k = 2 | 69.07 |
| kNN, k = 3 | 68.21 |

Since the feature vectors and hence the accuracy of the classification is dependent on the isolation of the correct LV contour for parametric fitting, the performance of LV contour identification was compared to alternative methods. To evaluate different segmentation methods, a clinical expert manually annotated the left ventricle from a dataset of 99 B-Mode Apical 4 Chamber view echo images (FIGS. 5A-F). The performance was compared to three techniques, namely, (a) Otsu thresholding alone without K-means clustering, (b) atlas-based segmentation, and (c), active shape models. The mean and standard deviation of Dice similarity $$\text{coefficient} = \frac{2|A \cap B|}{|A| + |B|}$$

as well as sensitivity and specificity as defined in Equations 4 and 5 below were used.

$$\text{sensitivity} = \frac{\text{true position}}{\text{true position} + \text{false negative}} \quad \text{Equation 4}$$

$$\text{specificity} = \frac{\text{true negative}}{\text{true negative} + \text{false positive}} \quad \text{Equation 5}$$

Figure 6:
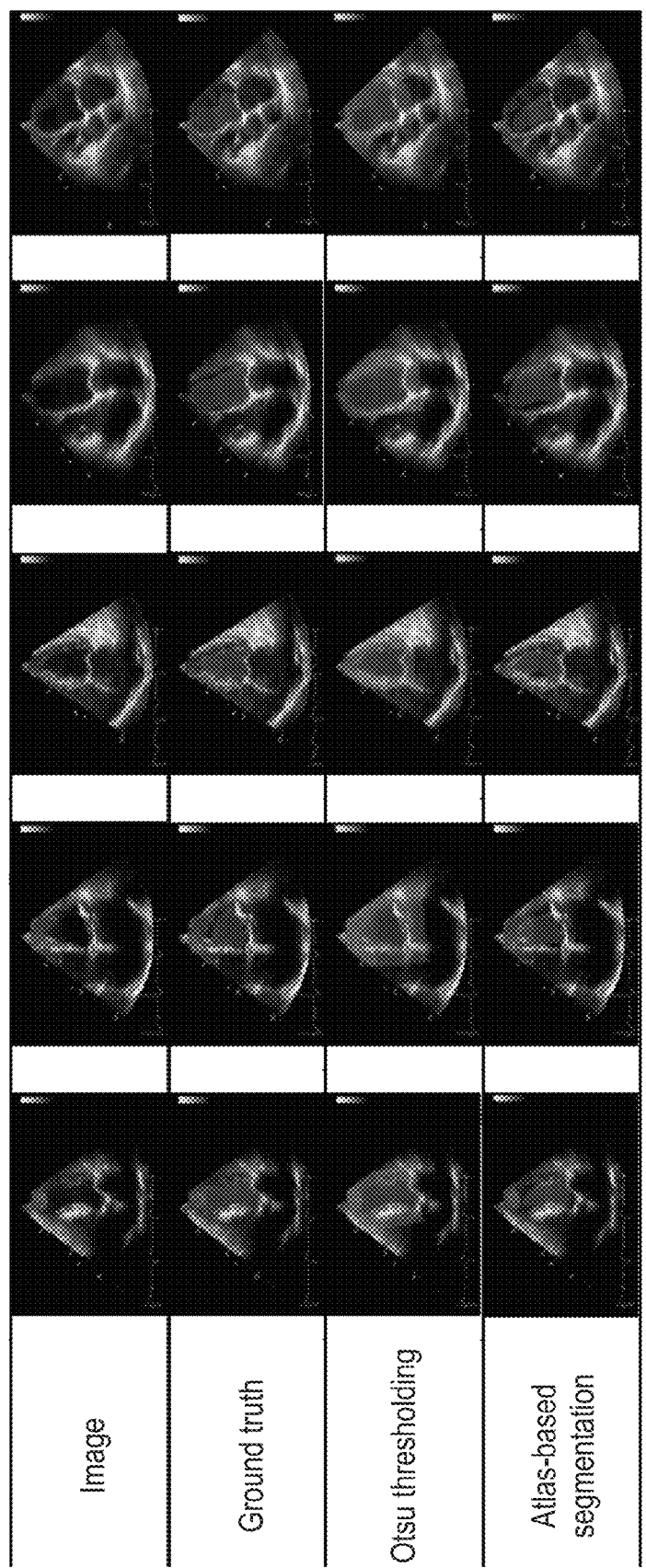
FIG. 6 depicts a plurality of exemplary left ventricle images, the corresponding ground truth, the results of Otsu thresholding, and the results of Atlas-based segmentation.
Figure 7:
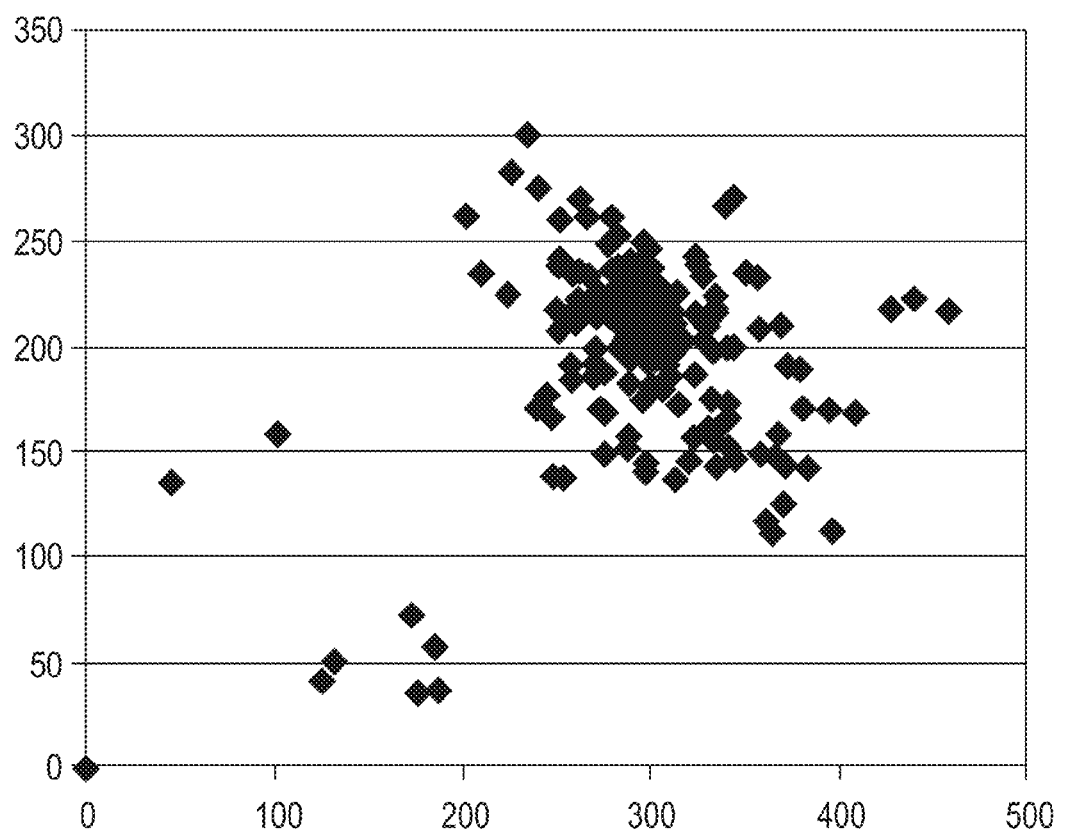
FIG. 7 illustrates spread in the estimate of the left ventricle centroid by active shape models according to embodiments of the present disclosure.

Here A and B represent the bounding contours of the ground truth and extracted contours, and $|A \cap B|$ is the number of matched points between contours. Results are given in Table 2, and depicted in FIG. 6. From these results, it may be seen that the LV bounding contour extraction according to the present disclosure gives the best overlap with the ground truth contours. Since the contours were unavailable from active shape model method, the performance was compared by measuring the deviation in the estimation of the LV centroid. Of the 503 sequences, the LV localization could be found for 189 cases using active shape models with an average spread in the localization over 200 pixels. The detailed localization spread is shown in FIG. 7. In comparison, the approaches described herein missed the LV localization in only 7 failure cases which were mostly due to early sector identification errors.

TABLE 2

| Method | DSC (%) | | Sensitivity (%) | | Specificity (%) | |
|---|---|---|---|---|---|---|
| | Mean | Std. | Mean | Std. | Mean | Std. |
| Otsu thresholding without Kmeans | 53.72 | 11.60 | 98.34 | 3.31 | 94.50 | 1.39 |
| Atlas-based segmentation | 69.90 | 18.70 | 68.65 | 21.10 | 99.25 | 0.71 |
| LV extraction, described herein | 89.12 | 10.2 | 82.9 | 12.4 | 97.02 | 0.1 |

In this paper we have presented a novel approach to discriminating between normal and abnormal left ventricular shapes by deriving feature vectors from the deviations in the parametric fits of distorted ellipses to left ventricular contours. Future work will address disease-specific segmentation of feature spaces.

Figure 8:
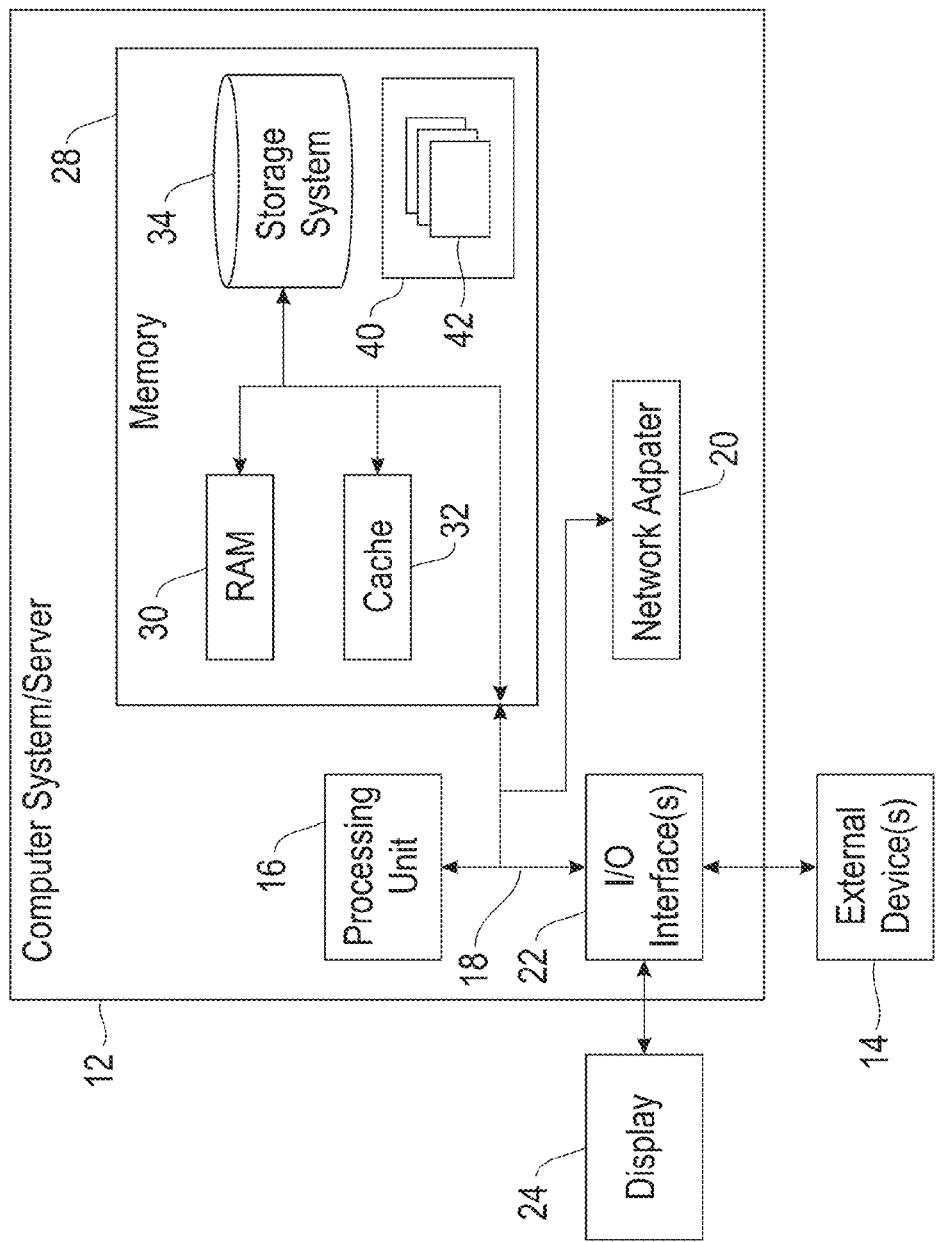
FIG. 8 depicts a computing node according to an embodiment of the present invention.

Referring now to FIG. 8, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 8, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   locating a first region of a first image of a heart by clustering, the first region depicting a chamber of the heart, the chamber having a chamber shape;
   determining a boundary of the first region by contour tracing and retaining the traced contour overlapping the located first region;
   comparing a predetermined shape to the boundary, the predetermined shape having been determined without reference to the first image;
   determining a first plurality of parameters that, when applied to the predetermined shape, conforms the predetermined shape to the boundary and minimizes at least one error between the predetermined shape and the boundary;
   providing the first plurality of parameters to a classifier; and
   receiving from the classifier an indication of normality or abnormality of the chamber shape.

2. The method of claim 1, wherein the image is an echocardiogram.

3. The method of claim 1, wherein the image includes a four-chamber view.

4. The method of claim 1, wherein the chamber is a left ventricle.

5. The method of claim 1, wherein the classifier is a linear classifier.

6. The method of claim 5, wherein the classifier is a support vector machine.

7. The method of claim 1, further comprising:
   determining a fit between the predetermined shape and the boundary; and
   providing the fit to the classifier.

8. The method of claim 1, wherein the predetermined shape is selected from the group consisting of: an ellipsoid, a spheroid and a distorted ellipse.

9. The method of claim 1, further comprising training the classifier, wherein training the classifier comprises:
providing a second plurality of parameters to the classifier, the second plurality of parameters corresponding to a second image of a normal heart; and
providing a third plurality of parameters to the classifier, the third plurality of parameters corresponding to a third image of an abnormal heart.

10. The method of claim 1, further comprising:
estimating the scale of the first image.

11. The method of claim 1, further comprising:
receiving a video; and
extracting the first image from the video.

12. The method of claim 11, further comprising:
extracting a plurality of additional images from the video.

13. The method of claim 1, further comprising:
locating a second region the first image of the heart, the second region comprising the first region and the second region depicting four chambers of the heart.

14. The method of claim 13, wherein locating the first region comprises:
thresholding the second region; and
determining the location of the first region within the second region.

15. The method of claim 14, wherein determining the location of the first region within the second region comprises:
performing k-means clustering.

16. The method of claim 1, wherein determining the first plurality of parameters comprises:
estimating a centroid of the boundary;
determining a dominant orientation of the boundary; and
using the dominant orientation to find a rotation.

17. The method of claim 1, wherein locating the first region of the first image of the heart comprises:
determining a dominant orientation within the first image; and
performing thresholding using the first image.

18. A computer program product for discriminating between normal and abnormal left ventricles in echocardiography, the computer program product comprising a computer readable storage medium having program instructions embodied therewith, the program instructions executable by a processor to cause the processor to:
locate a first region of a first image of a heart by clustering, the first region depicting a chamber of the heart, the chamber having a chamber shape;
determine a boundary of the first region by contour tracing and retaining the traced contour overlapping the located first region;
compare a predetermined shape to the boundary, the predetermined shape having been determined without reference to the first image;
determine a first plurality of parameters that, when applied to the predetermined shape, conforms the predetermined shape to the boundary and minimizes at least one error between the predetermined shape and the boundary;
provide the first plurality of parameters to a classifier; and
receive from the classifier an indication of normality or abnormality of the chamber shape.

19. The computer program product of claim 18, wherein locating the first region of the first image of the heart comprises:
determining a dominant orientation within the first image; and
performing thresholding using the first image.

20. A device comprising:
an imager configured to collect a first image of a heart;
an image analyzer configured to receive the first image of the heart, locate a first region of the heart by clustering, and determine a boundary of the first region of the first image by contour tracing and retaining the traced contour overlapping the located first region; the first region depicting a chamber of the heart, the chamber having a chamber shape;
a geometric fitter configured to determine a first plurality of parameters that, when applied to a predetermined shape, conforms the predetermined shape to the boundary of the first region and minimizes at least one error between the predetermined shape and the boundary, the predetermined shape having been determined without reference to the first image; and
a classifier configured to receive the first plurality of parameters and provide an indication of normality or abnormality of the chamber shape.

* * * * *